(12) United States Patent
Gupta et al.

(10) Patent No.: US 7,169,819 B2
(45) Date of Patent: Jan. 30, 2007

(54) PHARMACEUTICAL COMPOSITIONS OF FENRETINIDE HAVING INCREASED BIOAVAILABILITY AND METHODS OF USING THE SAME

(75) Inventors: Shanker Gupta, Rockville, MD (US); Barry J. Maurer, Sylmar, CA (US); C. Patrick Reynolds, Sherman Oaks, CA (US); B. Rao Vishnuvajjala, Rockville, MD (US)

(73) Assignee: Childrens Hospital Los Angeles, Los Angeles, CA (US)

( * ) Notice: Subject to any disclaimer, the term of this patent is extended or adjusted under 35 U.S.C. 154(b) by 0 days.

(21) Appl. No.: 10/010,914

(22) Filed: Dec. 5, 2001

(65) Prior Publication Data

US 2002/0183394 A1 Dec. 5, 2002

Related U.S. Application Data (60) Provisional application No. 60/251,463, filed on Dec. 5, 2000.

(51) Int. Cl.
*A61K 31/07* (2006.01)
*A61K 47/00* (2006.01)
*A61P 35/00* (2006.01)

(52) U.S. Cl. ............... 514/725; 514/728; 514/729; 514/731; 514/739; 514/772; 514/783; 514/937; 514/938; 514/975

(58) Field of Classification Search ............... 424/450; 514/725, 728, 729, 731, 739, 772, 783, 785, 514/786, 788, 936, 937, 938, 941, 943, 975
See application file for complete search history.

(56) References Cited

U.S. PATENT DOCUMENTS

| | | |
|---|---|---|
| 4,190,594 A | 2/1980 | Gander et al. |
| 4,323,581 A | 4/1982 | Gander |
| 4,665,098 A | 5/1987 | Gibbs et al. |
| 4,960,799 A | 10/1990 | Nagy |
| 5,464,870 A | 11/1995 | Veronesi et al. |
| 5,504,102 A | 4/1996 | Agharkar et al. |
| 5,599,953 A | 2/1997 | Curley, Jr. et al. |
| 5,663,377 A | 9/1997 | Curley, Jr. et al. |
| 5,767,146 A * | 6/1998 | Shudo et al. ............... 514/457 |
| 5,827,522 A | 10/1998 | Nowak |
| 5,925,776 A | 7/1999 | Nikolayev et al. |
| 6,267,985 B1 * | 7/2001 | Chen et al. ............... 424/451 |
| 6,294,192 B1 | 9/2001 | Patel et al. |
| 6,660,286 B1 * | 12/2003 | Lambert et al. ............ 424/405 |
| 2002/0143062 A1 * | 10/2002 | Lopez-Berestein et al. . 514/613 |

FOREIGN PATENT DOCUMENTS

| | | |
|---|---|---|
| WO | WO 98/57630 | 12/1998 |
| WO | WO00/00207 | 1/2000 |
| WO | WO 00/00207 | 1/2000 |

OTHER PUBLICATIONS

Product data sheet, TAXOL®, MeadJohnson Oncology Products (Jul. 2000).
Product data sheet, Sandimmune®, Novartis (Nov. 1999).
Technical Leaflet, Cremophor® EL, BASF (Jul. 1997).
Product data sheet, Cremophor® EL, BASF (Jul. 1999).
International Search Report for International Application Serial No. PCT/US01/46548 dated May 31, 2002.
Grit et al., "Chemical Stability of Liposomes: Implications for their Physical Stability," *Chemistry and Physics of Lipids*, 64, pp. 3-18 (1993).
Young et al., "Phospholid-Stabilized Nanoparticles of Cyclosporine A by Rapid Expansion from Supercritical to Aqueous Solution," *AAPS PharmSciTech 2003*; 5(1) Article 11 (http://www.aapspharmscitech.org).
"Product Development of Fenretinide, NSC 374551, Intravenous Formulation" European Journal of Cancer, Pergamon Press, Oxford, GB. vol. 38, p. S21 (Nov. 2002).
Supplementary European Search Report for European Patent Application No. 01 98 9170 mailed on Apr. 6, 2006.

* cited by examiner

*Primary Examiner*—Sreeni Padmanabhan
*Assistant Examiner*—Frank Choi
(74) *Attorney, Agent, or Firm*—Myers Bigel Sibley & Sajovec P.A.

(57) ABSTRACT

A pharmaceutical composition for parenteral delivery, comprising a retinide such as fenretinide in combination with a solvent capable of dispersing or solubilizing the retinide. The solvent comprises an alcohol, such as ethanol, in combination with an alkoxylated castor oil, such as CREMOPHOR® EL, or comprising a retinide, such as fenretinide, in an emulsion composed of a lipid dispersed in an aqueous phase, a stabilizing amount of a non-ionic surfactant, optionally a solvent, and optionally an isotonic agent. In addition, a method of use in the treatment of hyperproliferative disorders, such as cancers is described.

7 Claims, 1 Drawing Sheet

FIGURE 1.

Fenretinide Effects on Tumor Xenograft Growth

PHARMACEUTICAL COMPOSITIONS OF FENRETINIDE HAVING INCREASED BIOAVAILABILITY AND METHODS OF USING THE SAME

RELATED APPLICATIONS

The present application claims the benefit of provisional application Ser. No. 60/251,463; filed Dec. 5, 2000, the disclosure of which is incorporated by reference herein in its entirety.

FIELD OF THE INVENTION

The present invention concerns pharmaceutical compositions for parenteral delivery of a retinide such as fenretinide.

Background of the Invention Fenretinide [HPR; all-trans-N-(4-hydroxyphenyl)retinamide; CAS Registry number 65646-68-6] is a synthetic retinoic acid derivative having the structure:

Fenretinide is minimally soluble in aqueous solution. U.S. Pat. No. 4,665,098 by Gibbs describes an oral pharmaceutical composition of fenretinide as useful for the treatment of breast and bladder cancer. However, the bioavailability of this oral fenretinide composition is limited and greater anticancer effects might be obtained if fenretinide could be delivered intravenously to achieve higher drug plasma levels. Hence, there currently remains a need for new pharmacological compositions of fenretinide for parenteral, especially intravenous, administration which provide for both satisfactory solubility, and plasma and tissue bioavailability.

SUMMARY OF THE INVENTION

The present invention comprises pharmaceutical compositions of N-(4-hydroxyphenyl)retinamide (4-HPR), or analogs thereof (i.e., retinides), which may provide increased bioavailability of the active ingredient (the retinide). These may allow administration of significantly greater amounts of the active agents to patients, achieving greater plasma and tissue levels of drug as compared to administration of the same amount of drug in the currently available oral formulation (Gibbs), and may provide for a greater anticancer efficacy as a single agent, and in other anticancer drug combinations.

According to a first aspect of the invention, there are provided pharmaceutical compositions of the retinide in an alkoxylated castor oil (preferably a polyoxyethoxylated castor oil such as CREMOPHOR® EL). Preferably the composition also includes an alcohol such as ethanol. The compositions may be prepared from lyophilized retinide (preferably 4-HPR) or from non-lyophilized 4-HPR.

A second aspect of the present invention is pharmaceutical emulsion composition for parenteral delivery. The composition comprises, in combination:

(a) a hydrophilic phase (included in an amount to balance);

(b) a pharmacologically acceptable lipoid (i.e., oil) as a hydrophobic phase dispersed as particles in said hydrophilic phase (typically included in said composition in an amount of from 2 to 40 percent volume per volume);

(c) a retinide such as fenretinide (typically included in said composition in an amount of from 0.01 to 2 percent weight per volume);

(d) optionally, a solvent (typically included in said composition in an amount of from 0 to 10 percent volume per volume);

(e) from 0.01 to 10 percent weight per volume of a non-ionic surfactant in an amount sufficient to stabilize said emulsion (typically from about 0.01 to 10 percent weight per volume of said composition); and (f) optionally, an isotonic agent (typically included in said composition in an amount of from 0 to 10 percent weight per volume).

Methods of treating subjects afflicted with a hyperproliferative disorder by the parenteral administration of such compositions are also disclosed.

The foregoing and other objects and aspects of the present invention are explained in greater detail in the drawings herein and the specification set forth above.

DETAILED DESCRIPTION OF THE PREFERRED EMBODIMENTS

1. Retinides.

Retinides used for carrying out the present invention are, in general, ceramide-generating retinoids or retinoic acid derivatives. Such compounds include those described in U.S. Pat. No. 4,190,594 to Gander (the disclosures of all patent references cited herein are incorporated herein by reference). Ceramide-generating retinoids include all trans-retinoic acid (ATRA) and retinoic acid derivatives, including but not limited to:

(A) esters of all-trans-retinoic acid having the following formula:

wherein X is a member selected from the group consisting of:

2-cyclohexylethyl; 10-carbomethoxydecyl; 4-hydroxybutyl; cholesteryl; mixed m- and p-vinylbenzyl; and 4-bromobenzyl;

(B) esters of all-trans-retinoic acid having the following formula:

wherein Y is a member selected from the group consisting of: cholesteryloxy; phenyl; 4-bromophenyl; 4-methoxyphenyl; 4-nitrophenyl; 4-hydroxyphenyl; 4-methylphenyl; 4-cyanophenyl; 4-ethoxyphenyl; 4-acetoxyphenyl; 2-naphthyl; 4-biphenyl; 2,5-dimethoxyphenyl; 2,4-dichlorophenyl; 2,4-dimethylphenyl; 3,4-diacetoxyphenyl; 3,4,5-trimethoxyphenyl; and 2,4,6-trimethylphenyl; and (C) amides of all-trans-retinoic acid having the following formula:

wherein Z is a member selected from the group consisting of: n-propylamino; tert-butylamino; 1,1,3,3-tetramethylbutylamino; 1-morpholino; 4-hydroxyphenylamino; 4-carbomethoxy-2-hydroxyphenylamino; beta-(3,4-dimethoxyphenyl)-ethylamino; 2-benzothiazolylamino; 1-imidazolyl; 1-(2-nicotinoylhydrazolyl); 1-benzotriazolyl; 1-(1,2,4-triazolyl);

Particularly preferred is all-trans-N-(4-hydroxyphenyl)retinamide, also called fenretinide, which has CAS registry number 65646-68-6, and has the structure:

The foregoing compounds can be prepared in accordance with known techniques. See, e.g., U.S. Pat. No. 4,190,594 to Gander et al.; U.S. Pat. No. 4,665,098 to Gibbs.

Additional retinoic acid derivatives that can be used to carry out the present invention include C-Glycoside analogs of N-(4-hydroxyphenyl)retinamide-O-glucuronide. Such compounds and their preparation are known and described in U.S. Pat. Nos. 5,663,377 and 5,599,953, both to Curley et al., the disclosures of which are incorporated by reference herein in their entirety. Such compounds may have the general formula:

where R is COOH, $CH_2OH$, or H, and n is 0 or 1.

Specific examples of such compounds include: 4-(retinamido)phenyl-C-glucuronide; 4-(retinamido)phenyl-C-glucoside; 4-(retinamido)phenyl-C-xyloside; 4-(retinamido)benzyl-C-glucuronide; 4-(retinamido)benzyl-C-glucoside; 4-(retinamido)benzyl-C-xyloside; 1-(β-D-glucopyranosyl) retinamide; and 1-(D-glucopyranosyluronosyl)retinamide.

2. Alkoxylated Castor Oils and Compositions.

Alkoxylated castor oils are known and described in, for example, U.S. Pat. No. 5,827,522 and U.S. Pat. No. 5,504,102 to Agharkar et al. Applicants specifically intend that all U.S. patent references cited herein be incorporated herein by reference. Polyethoxylated castor oils are preferred.

Polyethoxylated castor oils such as described in U.S. Pat. No. 4,960,799 to Nagy and U.S. Pat. No. 5,925,776 to Nikolayev et al.

A particularly preferred polyethoxylated castor oil for carrying out the present invention is commercially available polyoxyl-35 castor oil, having a saponification value of 63 to 72, a hydroxyl value of 65 to 78, and an acid value <2, such as CREMOPHOR® EL (CTFA/INC: PEG-35 Castor Oil) (CAS Number 61791-12-6) from BASF Corp., 3000 Continental Drive—North, Mount Olive, N.J., 07828-1234 USA.

The alcohol employed in the solvent may be any suitable alcohol, but is preferably ethanol. In general, the solvent comprises from 30, 40, or 45 percent by volume up to 55, 60 or 70 percent by volume of the alkoxylated castor oil, and from 30, 40 or 45 percent by volume up to 55, 60 or 70 percent by volume of the alcohol. Alternatively, the solvent may be dehydrated ethanol employed at about 3.8 to 3.9 percent volume per volume. In one currently preferred embodiment, the solvent comprises 50 percent by volume of alkoxylated castor oil and 50 percent by volume of alcohol. The retinide is dispersed or solubilized in the solvent in any suitable amount, but is preferably dispersed or solubilized in an amount of at least 0.1, 1, 2 or 5 milligrams of retinide per milliliter of solvent, up to 15, 20, 30 or 40 milligrams of retinide per milliliter of solvent, or more.

The composition described above may be nonaqueous or aqueous. Water may be included in minor amounts, or may be added or combined with the composition in the form of a pharmaceutically acceptable carrier such as a saline solution or dextrose solution, whose combined composition is then administered to the patient. For example, a composition of the invention comprised of 10 mg/mL retinide solubilized in solvent may be combined with physiological saline solution or 5% dextrose solution for administration to a patient as a 1 mg/mL retinide solution.

3. Emulsion Compositions.

As noted above, a further aspect of the present invention is a pharmaceutical emulsion composition for parenteral delivery. In general, such a composition comprises, in combination:
 (a) a hydrophilic phase (included in an amount to balance);
 (b) from 2 to 40 percent volume per volume of a pharmacologically acceptable lipoid as a hydrophobic phase dispersed as particles in said hydrophilic phase;
 (c) from 0.01 or 0.1 to 0.5, 2 or 5 percent weight per volume of a retinide;
 (d) from 0 to 10 percent volume per volume of a solvent;
 (e) from 0.01 to 10 percent weight per volume of a non-ionic surfactant to stabilize said emulsion; and
 (f) from 0, 0.01, or 0.1 to 3, 6 or 10 percent weight per volume of an isotonic agent.

The composition preferably has a pH of about 5 to 10, and the particles in the composition are preferably from about 5 or 50 nanometers in diameter to about 400 or 1000 nanometers in diameter.

Any suitable pharmaceutically acceptable lipoid (or oil) may be used to carry out the invention, including but not limited to soybean oil, safflower oil, sunflower oil, borage oil, corn oil, olive oil, linseed oil, sesame oil, palm kernel oil, cotton seed oil, medium chain triglycerides from coconut oil distillates, black currant oil, and mixtures thereof. In general, the lipoid is preferably included in an amount of from about 10 to 30 percent volume per volume, and is preferably soybean oil.

In general, the solvent is absent, or present in an amount of at least 0.01 percent volume per volume. The solvent is used to dissolve the retinide prior to its addition to the oil to increase its solubility in the oil. Then the retinide-containing oil is homogenized into the aquous phase. At that point, it is believed that most of the solvent leaves the oil micelles (or other dispersed phase particles) and enters the aqueous phase, leaving the retinide in the oil micelle (as the water is much more polar than the oil, and ethanol is polar). Any suitable solvent may be employed, including but not limited to ethanol, dimethylsulfoxamide (DMSO), and ethyl acetamide (DMA). In a preferred embodiment, the solvent is ethanol and is included at about 0.01 to 5.0 percent volume per volume. Note that the solvent could be volatilized subsequent to addition of the retinide to the oil to remove the solvent therefrom.

Suitable non-ionic surfactants include but are not limited to egg phospholipids, polyoxyethylene fatty acid esters (Tweens), the block copolymers of polyoxypropylene and polyoxyethylene, also known as poloxamers, also known as Pluronics, combinations thereof, etc. In a preferred embodiment, the non-ionic surfactant is egg phospholipid at about 2 percent weight per volume.

Any suitable isotonic agent may be used. The isotonic agents when employed are typically used in amounts of about 0.8 to 8 percent weight per volume. These agents regulate the osmotic pressure to make the emulsion isotonic with the blood of the intended subject. Examples of isotonic agents include glycerin, and sugar alcohols such as xylitol, sorbitol, and mannitol. Other examples of isotonic agents include non-polar amino acids such as alanine, basic amino acids such as histidine, and/or uncharged polar amino acids such as glycine. Glycerine at about 1 percent weight per volume is currently preferred.

In a specific embodiment of the foregoing, the retinide is included in the composition at about 0.1 to 0.5 percent weight per volume, the solvent is dehydrated ethanol at 0.0 or 0.01 to 5.0 percent volume per volume, the amount of said lipoid is about 10 to 30 percent volume per volume, the amount of egg phospholipids is about 1 to 5 percent weight per volume, the isotonic agent is glycerin at about 1 percent weight per volume, and the pH is from 5 to 10.

The various ingredients described above may be combined and blended in accordance with known techniques for the preparation of emulsions and provided in a sterile package or vial for subsequent administration in accordance with known techniques, and as discussed further below.

4. Treatment and Administration.

The present composition can be administered for the treatment of hyperproliferative disorders such as tumors, cancers, and neoplastic disorders, as well as premalignant and non-neoplastic or non-malignant hyperproliferative disorders.

Subjects to be treated by the compositions and methods described herein are, in general, mammalian subjects, including both human subjects and animal subjects such as dogs, cats, horses, etc. for veterinary purposes.

Examples of tumors, cancers, and neoplastic tissue that can be treated by the present invention include but are not limited to malignant disorders such as breast cancers; osteosarcomas; angiosarcomas; fibrosarcomas and other sarcomas; leukemias; lymphomas; sinus tumors; ovarian, uretal, bladder, prostate and other genitourinary cancers; colon esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas.

Examples of premalignant and non-neoplastic or non-malignant hyperproliferative disorders include but are not limited to myelodysplastic disorders; cervical carcinoma-insitu; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions including arthritis. Also included are viral induced hyperproliferative diseases such as warts and EBV induced disease (i.e., infectious mononucleosis), scar formation, and the like. The methods of treatment disclosed herein may be employed with any subject known or suspected of carrying or at risk of developing a hyperproliferative disorder as defined herein.

As used herein, "treatment" of a hyperproliferative disorder refers to methods of killing, inhibiting or slowing the growth or increase in size of a body or population of hyperproliferative cells or tumor or cancerous growth, reducing hyperproliferative cell numbers, or preventing spread to other anatomic sites, as well as reducing the size of a hyperproliferative growth or numbers of hyperproliferative cells. As used herein, "treatment" is not necessarily meant to imply cure or complete abolition of hyperproliferative growths. As used herein, a treatment effective amount is an amount effective to result in the killing, the slowing of the rate of growth of hyperproliferative cells, the decrease in size of a body of hyperproliferative cells, and/or the reduction in number of hyperproliferative cells.

The therapeutically effective dosage of any one active agent, the use of which is in the scope of present invention, will vary somewhat from compound to compound, patient to patient, and will depend upon factors such as the condition of the patient and the route of delivery. Such dosages can be determined in accordance with routine pharmacological procedures known to those skilled in the art, particularly in light of the disclosure provided herein. For fenretinide, a dose to achieve a plasma level of about 1 $\mu$M to 10 or 50 $\mu$M, or greater, is employed.

The compositions described herein may be parenterally administered by any suitable technique, including intravenous, intraarterial, intrathecal, intramuscular, subcutaneous, and intraperitoneal injection or infusion.

The compositions described herein may be used in combination therapies, such as described in B. Maurer et al., PCT Application WO 00/00207 (6 Jan. 2000), and in B. Maurer et al., U.S. patent No. 6,368,831 (filed Dec. 23, 1999) (the disclosure of which is incorporated by reference herein in its entirety).

The present invention is explained in greater detail in the following non-limiting Examples.

EXAMPLE 1

Formulations in Diluent 12

Diluent 12 is a 50:50 v/v mixture of absolute alcohol (ethanol) and Cremophor EL, polyoxyethoxylated castor oil, USP. The drug can be easily dissolved in diluent 12 at a concentration of 10 mg/mL. It is possible to prepare solutions up to 15 mg/mL using 50/50 ethanol/Cremophor EL (diluent 12). Solutions with higher concentrations of fenretinide may be possible using a higher ratio of ethanol to Cremophor EL (ex: 55% ethanol: 45% Cremophor EL).

The 50:50 v/v ethanol/Cremophor EL (Diluent 12) drug solution is prepared by dissolving fenretinide in the required volume of alcohol with stirring and adding the appropriate amount of cremophor EL. The resulting solution is stable at refrigerated and room temperature for up to 3 months with no significant loss in potency or build-up of impurities. There is minimal loss of drug potency at accelerated temperatures such as 40 C, approximately 3% at the end of 3 months.

The above formulation can be conveniently diluted in 0.9% sodium chloride solution (Normal Saline, USP) or 5% dextrose solution, USP to yield 1 mg/mL solution, which is stable for 4 days with no loss in potency of the solution.

It is also possible to lyophilize the fenretinide formulations from t-butanol/water solutions. The concentration of t-butanol can be varied from 5% to 95%. The resulting amorphous powder can be reconstituted using Diluent 12 and further diluted in normally used infusion solutions such as normal saline and 5% dextrose. The lyophilized powder is stable at room temperature.

EXAMPLE 2

Emulsion Formulations of Fenretinide

Emulsion oil-in-water formulations of fenretinide were prepared using phospholipid. The formulation procedure is as follows.

The drug is dissolved in alcohol and added to the oil phase of the emulsion. An aqueous phase is prepared in a separate beaker by dispersing a batch quantity of egg phospholipid in water/glycerin solution. The pH of the aqueous phase is adjusted between 5–7 using sodium hydroxide. The aqueous phase is added to the oil phase by stirring. The resulting emulsion is homogenized to yield a oil/water emulsion with a final fenretinide concentration, variably, of 1 mg/ml (0.1%) or 2 mg/ml (0.2%), a final ethanol of 3.9% or 3.8%, respectively, a final egg phospholipid concentration of 2%, a final glycerin concentration of 1%, a pH of 7.2–7.4, and a particle size in the range of 50–400 nanometers.

The stability of these emulsions was monitored, and the emulsions found to be stable for over 1 month at refrigerated temperature with no change in potency and particle size. There is minimal change in particle size and potency at accelerated temperature such as room temperature.

EXAMPLE 3

Fenretinide Assay

The assay is a modification of the method of Formelli et al, (J Clin Oncol, 11:2036–2042, 1993). Concentrations of 4-HPR are measured by high performance liquid chromatography (HPLC). All procedures are performed under indirect yellow light. Stock standards are prepared in 1:1MeOH:

ACN and stored at −70° C. Quality assurance standards are prepared in normal heparinized plasma and stored at −70° C. Standards and QA and animal samples are prepared in silanized amber microtubes and kept in the dark and cold as much as possible. Plasma and tissues samples are extracted with MeOH:CAN for fenretinide administered oral (Gibbs formulation) or emulsified fenretinide delivered intraperitoneally. Plamsa samples taken from animals treated intraperetoneally with emulsified fenretinide were extracted with MeOH:chloroform:water to ensure emulsion disruption and release of fenretinide. Standard curve samples are prepared by spiking the appropriate amount of stock standards into 500 µL normal heparinized plasma containing the internal standard, N-(4-ethoxyphenyl)retinamide (4-EPR). Proteins are precipitated by adding 100 µL ice cold saturated potassium phosphate and 900 µL ice-cold acetonitrile. After centrifugation, supernatant is added to amber autoinjection vials and kept in the dark at room temperature until analyzed. 50 µL supernatant is injected into a Shimadzu liquid chromatograph system fitted with a Phenomenex Luna C18 (2) column and a Brownlee RP-18 precolumn. The mobile phase consists of acetonitrile:water:glacial acetic acid, (80:18:2, v/v/v) pumped at a flow rate of 1 mL/minute. Detection is performed at a wavelength of 340 nm, which allows good sensitivity for the retinoids of interest. Quality assurance and patient plasma samples are assayed in the same manner. Endogenous levels of retinol in the normal plasma complicates analysis, so a standard curve for retinol is prepared in 5% bovine serum albumin (BSA) and run as plasma samples.

EXAMPLES 4–10

Pharmacodynamic and Cytotoxicity Studies

Figure 1:
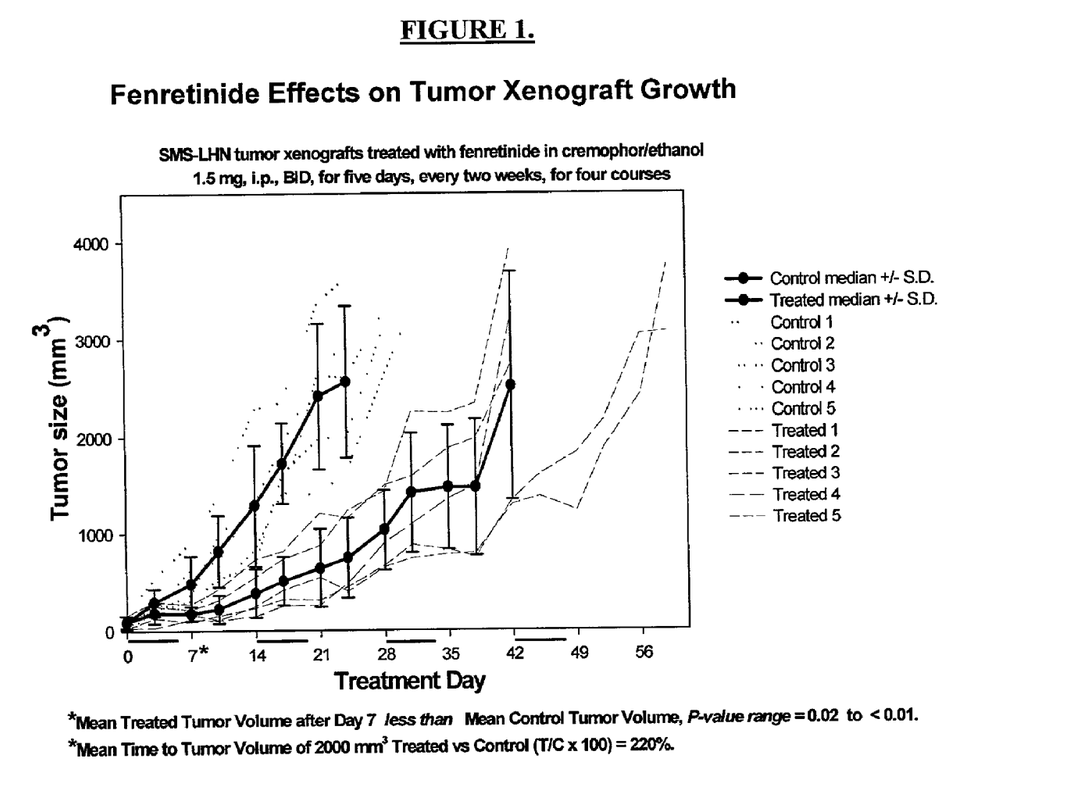
FIG. 1 illustrates that Fenretinide solubilized in cremophor/ethanol (50/50) as disclosed herein is effective in delaying the growth of human tumor xenografts grown in mice when given intraperitoneally. Immunocompromised (athymic) nude mice (ten) were injected subcutaneously with 50 million SMS-LHN human neuroblastoma tumor cells on their $3^{rd}$ serial passage to form murine tumor xenografts. Subcutaneous tumor xenografts were <175 mm$^3$ in size at the start of fenretinide injections. Nude mice (five) were injected intraperitoneally with fenretinide formulated as in Example 1. Mice were injected with 0.1 ml of fenretinide (15 mg/ml) in cremophor/ethanol (50/50) diluted with 0.3 ml NS prior to use (1.5 mg fenretinide in 0.4 ml volume), twice a day, for five days starting on Day 0, every 14 days, for four courses. Control mice (five) were injected with equal volumes of cremophor/ethanol, but without fenretinide, on the same schedule. Tumor xenografts were measured regularly, and tumor volume calculated as (0.5×height× width×length). Mice were sacrificed on the day that the tumor xenograft was measured as >3500 mm$^3$ or when tumor was necrotic. Mean volumes are graphed as +/− one standard deviation. Statistical significance of differences in means was evaluated by the unpaired, one-sided Student's t-test assuming unequal variance with the use of Microsoft© Excel 97 software. P values are two-sided. T/C values calculated at time until mean tumor volume (treated vs. control) was >2000 mm$^3$. T/C>200% indicates treatment highly active per accepted criteria.

Examples 4 to 10 are illustrated by Tables 1–3, FIG. 1, and Tables—4–6, respectively. These examples were carried out with the procedures generally described in Example 3 above. Examples 4–7 compare the administration of fenretinide solubilized in cremophor as described in Example 1 compared to administration of fenretinide according to the method of Gibbs, while examples 8–10 compare the administration of fenretinide containing emulsions as described in Example 2 compared to the administration of fenretinide according to the formulation of Gibbs.

Table 1 illustrates that of fenretinide solubilized in cremophor/ethanol (50/50) as disclosed herein achieved higher plasma levels when given intraperitoneally in mice for 2 or 4 days than an equal dose of fenretinide given orally (formulation of Gibbs) in mice for 5 days. Mice were either injected intraperitoneally (athymic/nude mice) with 1.5 mg fenretinide twice a day for 2 or 4 days, or feed 1.5 mg fenretinide orally (Balb/C mice) twice a day for 5 days. Animals were sacrificed and assayed 4 hours after their last dose. Plasma drug levels were assayed as above. Prior to fenretinide administration, immunocompromised (athymic) nude mice were injected subcutaneously with 5 million C6 rat glioma tumor cells, 50 million KCNR human neuroblastoma tumor cells, or 50 million SK-N-MC human primitive neuroectodermal tumor (PNET) cells, to form murine tumor xenografts. Subcutaneous tumor xenografts were approximately 200–400 mm$^3$ in size at the start of fenretinide injections. Nude mice (five or six each) injected with fenretinide in cremophor/ethanol (50/50), were sacrificed after 4 injections (2 days) or 8 injections (4 days). For intraperitoneal injections, 0.1 ml of fenretinide (15 mg/ml) in cremophor/ethanol (50/50) was diluted with 0.3 ml NS prior to use (1.5 mg fenretinide in 0.4 ml volume). For orally dosed mice, the contents of the currently-available oral fenretinide-containing capsules (formulated after the manner of Gibbs) were expressed and assayed for concentration of fenretinide as above. Mice were then feed 1.5 mg fenretinide in ~0.1 g of peanut butter twice a day, for five days, and then sacrificed. Tissue and/or tumor xenograft drug levels from these animals are reported in Table 2 and Table 3 (Example 5 and 6) below. Fenretinide has a reported half-life of ~12–16 hours in rodents (Kelloff, G. J., et al., (1994) "Clinical Development Plan: N-(4-hydroxyphenyl)retinamide." J Cell Biochem Suppl 20:176–96). Means are reported +/− one standard deviation. Statistical significance of differences in means was evaluated by the unpaired, one-sided Student's t-test assuming unequal variance with the use of Microsoft© Excel 97 software. All P values are one-sided.

Table 2 illustrates that fenretinide solubilized in cremophor/ethanol (50/50) as disclosed herein achieved higher tissue levels when delivered intraperitoneally for 2 or 4 days in mice than an equal dose of fenretinide given orally (formulation of Gibbs) in mice for 5 days. Mice were either injected intraperitoneally (athymic/nude mice) with 1.5 mg fenretinide twice a day for 2 or 4 days, or feed 1.5 mg fenretinide orally (Balb/C mice) twice a day for 5 days. Animals were sacrificed and assayed 4-hours after their last dose. Tissue drug levels were assayed as above. Prior to fenretinide administration, immunocompromised (athymic) nude mice were injected subcutaneously with 5 million C6 rat glioma tumor cells, 50 million KCNR human neuroblastoma tumor cells, or 50 million SK-N-MC human primitive neuroectodermal tumor (PNET) cells, to form murine tumor xenografts. Subcutaneous tumor xenografts were approximately 200–400 mm$^3$ in size at the start of fenretinide injections. Details of drug delivery is given in Table 1 (Example 4) above. Tissue and tumor xenograft data are from the same mice upon which plasma data is reported in Table 1 (Example 4) above. Fenretinide has a reported half-life of ~12–16 hours in rodents (Kelloff, G. J., et al., (1994) "Clinical Development Plan: N-(4-hydroxyphenyl) retinamide." J Cell Biochem Suppl 20:176–96). Means are reported +/− one standard deviation. Statistical significance of differences in means was evaluated by the unpaired Student's t-test assuming unequal variance with the use of Microsoft© Excel 97 software. All P values are one-sided.

Table 3 illustrates that fenretinide solubilized in cremophor/ethanol (50/50) as disclosed herein obtained drug levels in tumor xenografts when delivered intrperitoneally in mice for eithe 2 or 4 days. Mice (athymic/nude) were injected intraperitoneally with 1.5 mg fenretinide twice a day for 2 or 4 days. Animals were sacrificed and assayed 4 hours after their last dose. Tissue drug levels were assayed as above. Prior to fenretinide administration, immunocompromised nude mice were injected subcutaneously with 5 million C6 rat glioma tumor cells, 50 million KCNR human neuroblastoma tumor cells, or 50 million SK-N-MC human primitive neuroectodermal tumor (PNET) cells, to form murine xenografts. Subcutaneous tumor xenografts were approximately 200–400 mm$^3$ in size at the start of fenretinide injections. Details of drug delivery is given in Table 1 (Example 4) above. Tissue and tumor xenograft data are from the same mice upon which plasma data is reported in Table 1 (Example 4) above. Fenretinide has a reported half-life of ~12–16 hours in rodents (Kelloff, G. J., et al., (1994) "Clinical Development Plan: N-(4-hydroxyphenyl) retinamide." J Cell Biochem Suppl 20:176–96. Means are reported +/− one standard deviation.

Fenretinide solubilized in cremophor/ethanol (50/50) as disclosed herein is effective in delaying the growth of human tumor xenografts grown in mice when given intraperitoneally as shown in FIG. 1. Immunocompromised (athymic) nude-mice (ten) were injected subcutaneously with 50 million SMS-LHN human neuroblastoma tumor cells on their $3^{rd}$ serial passage to form murine tumor xenografts. Subcutaneous tumor xenografts were <175 mm³ in size at the start of fenretinide injections. Nude mice (five) were injected intraperitoneally with fenretinide formulated as in Example 1. Mice were injected with 0.1 ml of fenretinide (15 mg/ml) in cremophor/ethanol (50/50) diluted with 0.3 ml NS prior to use (1.5 mg fenretinide in 0.4 ml volume), twice a day, for five days starting on Day 0, every 14 days, for four courses. Control mice (five) were injected with equal volumes of cremophor/ethanol, but without fenretinide, on the same schedule. Tumor xenografts were measured regularly, and tumor volume calculated as (0.5×height×width×length). Mice were sacrificed on the day that the tumor xenograft was measured as >3500 mm3 or when tumor was necrotic. Mean volumes are graphed as +/− one standard deviation. Statistical significance of differences in means was evaluated by the unpaired, one-sided Student's t-test assuming unequal variance with the use of Microsoft© Excel 97 software. P values are two-sided. T/C values calculated at time until mean tumor volume (treated vs. control) was >2000 mm³. T/C >200% indicates treatment highly active per accepted criteria.

Table 4 illustrates that fenretinide-containing emulsions as disclosed herein achieved higher fenretinide plasma levels in mice when given intraperitoneally than a greater dose of fenretinide when given orally (formulation of Gibbs). Mice (athymic/nude mice) were either injected intraperitoneally (i.p.) with the fenretinide-containing emulsion of Example 2 (2 mg/ml) (1.0 mg fenretinide, i.p., twice a day, for 2 or 4 days), or mice (Balb/C mice) were feed the oral fenretinide formulation of Gibbs (1.5 mg, orally, twice a day, for 5 days). Animals were sacrificed and assayed 4 hours after their last dose. Fenretinide plasma levels were assayed as above. Mice injected with emulsified fenretinide were sacrificed after 4 injections (2 days) or 8 injections (4 days). For orally dosed mice, the contents of fenretinide-containing capsules formulated after the manner of Gibbs were expressed and assayed for concentration of fenretinide as above. Mice were then feed 1.5 mg fenretinide in ~0.1 g of peanut butter, twice a day, for five days, and then sacrificed. Fenretinide plasma levels resulting from the administration of the emulsified fenretinide of Example 2 and the oral formulation of Gibbs are compared in Table 4. Tissue levels from these animals are reported in Table 5 (Example 9) below. Fenretinide has a reported half-life of ~12–16 hours in rodents (Kelloff, G. J., et al., (1994) "Clinical Development Plan: N-(4-hydroxyphenyl)retinamide." J Cell Biochem Suppl 20:176–96). Statistical significance of differences in means was evaluated by the unpaired Student's t-test assuming unequal variance with the use of Microsoft© Excel 97 software. P values are one-sided.

Table 5 illustrates that fenretinide-containing emulsions as disclosed herein achieved higher tissue levels when delivered intraperitoneally in mice than a greater dose of fenretinide given orally (formulation of Gibbs). Mice (athymic/nude mice) were injected intraperitoneally with the fenretinide-containing emulsion of Example 2 (2 mg/ml) (1.0 mg fenretinide, i.p., twice a day, for 2 or 4 days), or mice (Balb/C mice) were feed the oral fenretinide formulation of Gibbs (1.5 mg, orally, twice a day, for 5 days). Animals were sacrificed and assayed 4 hours after their last dose. Fenretinide tissue levels were assayed as above. Mice injected with emulsified fenretinide were sacrificed after 4 injections (2 days) or 8 injections (4 days). For orally dosed mice, the contents of fenretinide-containing capsules formulated after the manner of Gibbs were expressed and assayed for concentration of fenretinide as above. Mice were then feed 1.5 mg fenretinide in ~0.1 g of peanut butter twice a day, for five days, and then sacrificed. Fenretinide tissue levels resulting from the administration of the emulsified fenretinide of Example 2 and the oral formulation of Gibbs are compared in Table 5. Fenretinide has a reported half-life of ~12–16 hours in rodents (Kelloff, G. J., et al., (1994) "Clinical Development Plan: N-(4-hydroxyphenyl)retinamide." J Cell Biochem Suppl 20:176–96). Statistical significance of differences in means was evaluated by the unpaired Student's t-test assuming unequal variance with the use of Microsoft© Excel 97 software. P values are one-sided.

Table 6 illustrates that fenretinide-containing emulsions as disclosed herein obtained drug levels in murine cancer xenografts when delivered intraperitoneally. Five days prior to fenretinide administration, immunocompromised (athymic) nude mice were injected subcutaneously with 5 million C6 rat glioma tumor cells. Subcutaneous tumor xenografts were approximately 300–400 mm3 in size at the start of fenretinide injections. Mice (athymic/nude mice) were injected intraperitoneally with the fenretinide-containing emulsion of Example 2 (2 mg/ml) (1.0 mg fenretinide, i.p., twice a day) for 2 or 4 days. Animals were sacrificed and assayed 4 hours after their last dose. Tumor xenograft drug levels were assayed as above, and are demonstrated in TABLE 6. Tumor xenograft data are from the same mice for which plasma and tissue data are reported in Tables 4 and 5 (Examples 8 and 9) above. Fenretinide has a reported half-life of ~12–16 hours in rodents (Kelloff, G. J., et al., (1994) "Clinical Development Plan: N-(4-hydroxyphenyl) retinamide." J Cell Biochem Suppl 20:176–96).

TABLE 1

Fenretinide Levels in Plasma
Cremophor/ethanol, 1.5 mg fenretinide, ip.,
twice a day, for 2 or 4 days
vs. Oral (Gibbs formulation), 1.5 mg fenretinide, p.o.,
twice a day, for 5 days

| mouse | C6 Xenograft Plasma Levels (uM) i.p. cremophor/ethanol | |
|---|---|---|
| | Day 2 | Day 4 |
| 1 | 0.7 | 23.8 |
| 2 | 27.0 | 12.6 |
| 3 | 14.7 | 15.5 |
| 4 | 27.5 | 17.0 |
| 5 | 10.1 | 15.6 |
| 6 | | 43.6 |
| mean | 16 +/− 11 | 21 +/− 12* |

*Day 2 i.p levels > Day 5 oral levels, P = 0.02
*Day 4 i.p. levels > Day 5 oral levels, P < 0.01

| mouse | KCNR Xenograft Plasma Levels (uM) i.p. cremophor/ethanol | |
|---|---|---|
| | Day 2 | Day 4 |
| 1 | 45.6 | 48.6 |
| 2 | 201.1 | 17.8 |
| 3 | 22.3 | 218.0 |
| 4 | 31.5 | 3.2 |
| 5 | 20.4 | 64.2 |
| mean | 64 +/− 77 | 70 +/− 86** |

**Day 2 i.p levels > Day 5 oral levels, P = 0.07
**Day 4 i.p levels > Day 5 oral levels, P = 0.07

TABLE 1-continued

Fenretinide Levels in Plasma
Cremophor/ethanol, 1.5 mg fenretinide, ip.,
twice a day, for 2 or 4 days
vs. Oral (Gibbs formulation), 1.5 mg fenretinide, p.o.,
twice a day, for 5 days SK-N-MC Xenograft Plasma Levels (uM)
i.p. cremophor/ethanol

| mouse | Day 2 | Day 4 |
|---|---|---|
| 1 | 0.2 | 151.2 |
| 2 | 11.5 | 225.8 |
| 3 | 20.7 | 32.2 |
| 4 | 48.8 | 66.4 |
| 5 | 12.8 | 108.7 |
| mean | 19 +/− 18 | 117 +/− 76*** |

***Day 2 i.p levels > Day 5 oral levels, P = 0.05
***Day 4 i.p levels > Day 5 oral levels, P = 0.01

Plasma Levels (uM)
Oral (Gibbs formulation)

| mouse | Day 5 |
|---|---|
| 1 | 1.5 |
| 2 | 1.5 |
| 3 | 2.0 |
| 4 | 1.4 |
| 5 | 1.5 |
| mean | 1.6 +/− 0.2 |

TABLE 2

Fenretinide Levels in Tissues
Cremophor/ethanol, 1.5 mg fenretinide, i.p.,
twice a day, for 2 or 4 days
vs. Oral (Gibbs formulation), 1.5 mg fenretinide, p.o.,
twice a day, for 5 days BRAIN LEVELS (ug/g)

C6 i.p. cremophor/ethanol

| mouse | Day 2 | Day 4 |
|---|---|---|
| 1 | 4.1 | 14.3 |
| 2 | 0.8 | 9.7 |
| 3 | 6.4 | 8.3 |
| 4 | 6.8 | 3.8 |
| 5 | 7.2 | 7.6 |
| 6 | | 10.4 |
| mean | 5.1 +/− 2.7* | 9 +/− 3.5* |

*Day 2 i.p. levels > Day 5 oral levels, P = 0.05
*Day 4 i.p. levels > Day 5 oral levels, P = 0.01

KNCR i.p. cremophor/ethanol

| mouse | Day 2 | Day 4 |
|---|---|---|
| 1 | 9.1 | 2.2 |
| 2 | 10.4 | 3 |
| 3 | 6.1 | 6.4 |
| 4 | 8.7 | 2 |
| 5 | 2.1 | 2.4 |
| mean | 7.3 +/− 3.3 | 3.2 +/− 1.8** |

**Day 2 i.p. levels > Day 5 oral levels, P = 0.02
**Day 4 i.p. levels > Day 5 oral levels, P = 0.22

SKNMC i.p. cremophor/ethanol

| mouse | Day 2 | Day 4 |
|---|---|---|
| 1 | 1.5 | 6.4 |
| 2 | 11.5 | 7.4 |
| 3 | 2.2 | 8.2 |

TABLE 2-continued

Fenretinide Levels in Tissues
Cremophor/ethanol, 1.5 mg fenretinide, i.p.,
twice a day, for 2 or 4 days
vs. Oral (Gibbs formulation), 1.5 mg fenretinide, p.o.,
twice a day, for 5 days

| | | |
|---|---|---|
| 4 | 5.5 | 10.2 |
| 5 | 7.9 | 10 |
| mean | 5.7 +/− 4.1 | 8.4 +/− 1.6*** |

***Day 2 i.p. levels > Day 5 oral levels, P = 0.08
***Day 4 i.p. levels > Day 5 oral levels, P < 0.01

Oral (Gibbs)

| mouse | Day 5 |
|---|---|
| 1 | 2.8 |
| 2 | 2.4 |
| 3 | 3.2 |
| 4 | 2.6 |
| 5 | 1.4 |
| mean | 2.4 +/− 0.7 |

LIVER LEVELS (ug/g)

C6 i.p. cremophor/ethanol

| mouse | Day 2 | Day 4 |
|---|---|---|
| 1 | 6 | 44.5 |
| 2 | 24.4 | 39.3 |
| 3 | 39.9 | 52.9 |
| 4 | 43 | 48.6 |
| 5 | 27.6 | 48.2 |
| 6 | | 44.5 |
| mean | 28 +/− 15 | 46 +/− 5* |

*Day 2 i.p. levels > Day 5 oral levels, P < 0.01
*Day 4 i.p. levels > Day 5 oral levels, P < 0.01

KNCR i.p. cremophor/ethanol

| mouse | Day 2 | Day 4 |
|---|---|---|
| 1 | 74.4 | 40.7 |
| 2 | 138.6 | 35.6 |
| 3 | 43.7 | 37.6 |
| 4 | 52.1 | 15.3 |
| 5 | 30.7 | 21.8 |
| mean | 68 +/− 42 | 30 +/− 11** |

**Day 2 i.p. levels > Day 5 oral levels, P = 0 01
**Day 4 i.p. levels > Day 5 oral levels, P < 0 01

SKNMC i.p. cremophor/ethanol

| mouse | Day 2 | Day 4 |
|---|---|---|
| 1 | 1.7 | 68.4 |
| 2 | 17.5 | 55.5 |
| 3 | 38.1 | 46.8 |
| 4 | 68.1 | 49.7 |
| 5 | 36.8 | 59.7 |
| mean | 33 +/− 25 | 56 +/− 9*** |

***Day 2 i.p. levels > Day 5 oral levels, P = 0.03
***Day 4 i.p. levels > Day 5 oral levels, P < 0.01

Oral (Gibbs)

| mouse | Day 5 |
|---|---|
| 1 | 22.1 |
| 2 | 12.7 |
| 3 | 22.7 |
| 4 | 5.5 |
| 5 | 23.2 |
| mean | 17 +/− 8 |

TABLE 3

Fenretinide Levels in Tumor Xenografts
Cremophor/ethanol, 1.5 mg fenretinide, p.,
twice a day, for 2 or 4 days
Fenretinide Level in Tumor Xenografts (ug/g)

C6

| mouse | Day 2 | Day 4 |
|---|---|---|
| 1 | 2.7 | 21.4 |
| 2 | 14.1 | 14.9 |
| 3 | 20.9 | 17.3 |
| 4 | 16.9 | 18.9 |
| 5 | 11.8 | 19.1 |
| 6 |  | 23.3 |
| mean | 13.3 +/− 6.8 | 19.2 +/− 3.0 |

KNCR

| mouse | Day 2 | Day 4 |
|---|---|---|
| 1 | 25.4 | 5.8 |
| 2 | 23.3 | 8 |
| 3 | 10.2 | 10.4 |
| 4 | 15.5 | 3.6 |
| 5 | 17.2 | 12.5 |
| mean | 18.3 +/− 6.1 | 8.1 +/− 3.5 |

SK-N-MC

| mouse | Day 2 | Day 4 |
|---|---|---|
| 1 | 0.6 | 12.1 |
| 2 | 13.6 | 9.9 |
| 3 | 10.2 | 16.4 |
| 4 | 9.8 | 14.7 |
| 5 | 9.1 | 17.9 |
| mean | 8.7 +/− 4.8 | 14.2 +/− 3.2 |

TABLE 4

Fenretinide Levels in Plasma
(Oral (Gibbs formulation) at 1.5 mg fenretinide, twice a day, for 5 days)
(Emulsion at 1.0 mg fenretinide, twice a day, for 2 or 4 days)

PLASMA LEVELS - DAY 2
i.p. Emulsion

| mouse | μM |
|---|---|
| 1 | 10.0 |
| 2 | 33.9 |
| 3 | 6.9 |
| 4 | 10.5 |
| 5 | 6.9 |
| mean | 13.4 +/− 11.6* |

*Day 2 Emulsion > Day 5 oral, P = 0.04.

PLASMA LEVELS - DAY 4
i.p. Emulsion

| mouse | μM |
|---|---|
| 1 | 1.8 |
| 2 | 5.1 |
| 3 | 16.7 |
| 4 | 3.2 |
| 5 | 1.9 |
| 6 | 1.3 |
| mean | 5.0 +/− 5.9** |

**Day 4 Emulsion > Day 5 oral, P = 0.1.

TABLE 4-continued

Fenretinide Levels in Plasma
(Oral (Gibbs formulation) at 1.5 mg fenretinide, twice a day, for 5 days)
(Emulsion at 1.0 mg fenretinide, twice a day, for 2 or 4 days)

PLASMA LEVELS - DAY 5
oral (Gibbs formulation)

| mouse | μM |
|---|---|
| 1 | 1.5 |
| 2 | 1.5 |
| 3 | 2.0 |
| 4 | 1.4 |
| 5 | 1.5 |
| mean | 1.6 +/− 0.24*** |

TABLE 5

Fenretinide Levels in Tissues
(Oral (Gibbs formulation) at 1.5 mg fenretinide, twice a day, for 5 days)
(Emulsion at 1.0 mg fenretinide, twice a day, for 2 or 4 days)

| | i.p. emulsion | | oral (Gibbs formulation) | |
|---|---|---|---|---|
| mouse | Day 2 | Day 4 | mouse | Day 5 |

BRAIN LEVELS (ug/g)

| 1 | 5.1 | 2.5 | 1 | 2.8 |
|---|---|---|---|---|
| 2 | 4 | 6.5 | 2 | 2.4 |
| 3 | 3.1 | 4.3 | 3 | 3.2 |
| 4 | 9.5 | 4.6 | 4 | 2.6 |
| 5 | 3.7 | 2.4 | 5 | 1.4 |
| 6 |  | 1.8 | mean | 2.5 +/− 0.7* ** |
| mean | 5.1 +/− 2.6* | 3.7 +/11.8** | | |

*Day 2 Emulsion > Day 5 oral P = 0.04.
**Day 4 Emulsion > Day 5 oral, P = 0.08.

LIVER LEVELS(ug/g)

| 1 | 32.9 | 14.4 | 1 | 22.1 |
|---|---|---|---|---|
| 2 | 33 | 39.1 | 2 | 12.7 |
| 3 | 28.5 | 30.2 | 3 | 22.7 |
| 4 | 53.2 | 36.1 | 4 | 5.5 |
| 5 | 33 | 36.4 | 5 | 23.2 |
| 6 |  | 40.4 | mean | 17.2 +/− 8* ** |
| mean | 36.1 +/− 9.7* | 32.8 +/− 9.7** | | |

*Day 2 Emulsion > Day 5 oral, P < 0.01.
**Day 4 Emulsion > Day 5 oral, P < 0.01.

TABLE 6

Fenretinide Levels in Murine Tumor Xenografts
(fenretinide emulsion, 1.0 mg, i.p., twice a day, for 2 or 4 days)
C6 Glioma Xenograft Levels (ug/g)
i.p. Emulsion

| mouse | Day 2 | Day 4 |
|---|---|---|
| 1 | 9.9 | 4.5 |
| 2 | 7.1 | 10.3 |
| 3 | 9.7 | 7.3 |
| 4 | 28.8 | 7.3 |
| 5 | 7.6 | 9.3 |
| 6 |  | 7.5 |
| mean | 12.6 +/− 9.1 | 7.7 +/− 2.0 |

The foregoing is illustrative of the present invention, and is not to be construed as limiting thereof. The invention is defined by the following claims, with equivalents of the claims to be included therein.

That which is claimed is:

1. A pharmaceutical emulsion composition for parenteral delivery, said composition consisting essentially of, in combination:
   (a) a hydrophilic phase;
   (b) from about 2 to 40 percent volume per volume of a pharmacologically acceptable lipoid as a hydrophobic phase dispersed as particles in said hydrophilic phase, wherein said lipoid is soybean oil, and wherein said particles are from 5 to 1000 nanometers in diameter;
   (c) from about 0.01 to 2 percent weight per volume of fenretinide;
   (d) from about 0.01 to 10 percent volume per volume of ethanol;
   (e) from about 0.01 to 10 percent weight per volume of a surfactant to stabilize said emulsion composition, wherein said surfactant is selected from egg phospholipids; and
   (f) from about 1 to 10 percent weight per volume of glycerin;
   said emulsion composition having a pH of about 5 to 10.

2. The composition of claim 1 wherein fenretinide is present at about 0.1 to 0.5 percent weight per volume.

3. The composition of claim 1 wherein ethanol is present at about 0.01 to 5.0 percent volume per volume.

4. The composition of claim 1 wherein the egg phospholipid is present at about 2 percent weight per volume.

5. The composition of claim 1 wherein the glycerin is present in an amount of about 1 to 3 percent weight per volume.

6. The composition of claim 1 wherein said particles are from 50 to 400 nanometers in diameter.

7. The composition of claim 1 wherein:
   fenretinide is present at about 0.1 to 0.5 percent weight per volume;
   ethanol is present at about 0.01 to 5.0 percent volume per volume;
   egg phospholipid is present at about 2 percent weight per volume;
   glycerin is present in an amount of about 1 to 3 percent weight per volume; and
   said particles are from 50 to 400 nanometers in diameter.

* * * * *

UNITED STATES PATENT AND TRADEMARK OFFICE
CERTIFICATE OF CORRECTION

PATENT NO.         : 7,169,819 B2
APPLICATION NO. : 10/010914
DATED              : January 30, 2007
INVENTOR(S)        : Gupta et al.

Page 1 of 1

It is certified that error appears in the above-identified patent and that said Letters Patent is hereby corrected as shown below:

Col. 1 Line 4-5
Please Add the required government support clause:
--This invention was made with government support under contract number CA081403 awarded by the National Cancer Institute. The government has certain rights in the invention.--

Signed and Sealed this

Sixth Day of November, 2007

JON W. DUDAS
*Director of the United States Patent and Trademark Office*